US010028895B2

(12) United States Patent
Bergeron et al.

(10) Patent No.: US 10,028,895 B2
(45) Date of Patent: Jul. 24, 2018

(54) EMULSION STABILIZATION VIA SILICILIC ACID COMPLEXATION

(71) Applicant: L'Oreal, Paris (FR)

(72) Inventors: Vance Bergeron, Francheville (FR); Jean-Thierry Simonnet, Mamaroneck, NY (US); Florence Levy, Paris (FR); Aurelie LaFuma, Paris (FR); Stephane Santucci, Lyons (FR)

(73) Assignee: L'OREAL, Paris (FR)

( * ) Notice: Subject to any disclaimer, the term of this patent is extended or adjusted under 35 U.S.C. 154(b) by 272 days.

(21) Appl. No.: 13/896,646

(22) Filed: May 17, 2013

(65) Prior Publication Data
US 2014/0341981 A1    Nov. 20, 2014

(51) Int. Cl.
| A61K 8/06 | (2006.01) |
| C11B 9/00 | (2006.01) |
| A23D 7/02 | (2006.01) |
| A61K 8/25 | (2006.01) |
| A61K 8/37 | (2006.01) |
| A61K 8/41 | (2006.01) |
| A61K 8/44 | (2006.01) |
| A61Q 19/00 | (2006.01) |
| A61K 9/107 | (2006.01) |
| A61K 47/02 | (2006.01) |

(52) U.S. Cl.
CPC ............. *A61K 8/062* (2013.01); *A23D 7/02* (2013.01); *A61K 8/25* (2013.01); *A61K 8/37* (2013.01); *A61K 8/416* (2013.01); *A61K 8/44* (2013.01); *A61Q 19/00* (2013.01); *C11B 9/00* (2013.01); *A61K 9/107* (2013.01); *A61K 47/02* (2013.01)

(58) Field of Classification Search
CPC ........ A01N 33/12; A61K 8/416; A61K 31/14; A61K 2800/5426; A61K 47/186; A61K 47/18
See application file for complete search history.

(56) References Cited

U.S. PATENT DOCUMENTS

| 3,661,602 A | 5/1972 | Gerow |
| 3,725,095 A | 4/1973 | Weidman et al. |
| 3,929,678 A | 12/1975 | Laughlin et al. |
| 5,725,875 A * | 3/1998 | Noll ............... A01N 25/24 |
| | | 424/1.17 |
| 5,900,394 A * | 5/1999 | Goel ............... A61K 8/062 |
| | | 510/141 |
| 6,107,358 A | 8/2000 | Harada et al. |
| 6,159,453 A | 12/2000 | Avnir et al. |
| 6,238,650 B1 | 5/2001 | Lapidot et al. |
| 6,248,315 B1 | 6/2001 | Young et al. |
| 6,620,407 B1 | 9/2003 | Gers-Barlag et al. |
| 6,677,389 B2 | 1/2004 | Fukuda et al. |
| 7,670,999 B2 | 3/2010 | Sebillotte-Arnaud et al. |
| 2002/0192180 A1 | 12/2002 | Fairley et al. |
| 2004/0241120 A1 | 12/2004 | Pataut et al. |
| 2007/0258933 A1 | 11/2007 | Bui et al. |
| 2007/0258934 A1 | 11/2007 | Bui et al. |
| 2007/0275257 A1 | 11/2007 | Muraguchi et al. |
| 2007/0292676 A1 | 12/2007 | Naigertsik et al. |
| 2008/0199526 A1 | 8/2008 | Poschalko et al. |
| 2009/0325780 A1 | 12/2009 | Gauckler et al. |
| 2010/0135938 A1* | 6/2010 | Ishikubo ............ A61K 8/062 |
| | | 424/59 |
| 2011/0158923 A1 | 6/2011 | Galeone et al. |
| 2011/0293677 A1 | 12/2011 | Bekemeier et al. |
| 2011/0311723 A1 | 12/2011 | Bekemeier et al. |

FOREIGN PATENT DOCUMENTS

| DE | 19834819 A1 | 2/2000 | |
| EP | 0107199 A2 | 5/1984 | |
| EP | 1038573 A2 | 9/2000 | |
| EP | 1627668 A1 | 2/2006 | |
| EP | 1759690 A2 | 3/2007 | |
| EP | 2436452 A1 | 4/2012 | |
| GB | 2131820 A | 6/1984 | |
| JP | S627632 A | 1/1987 | |
| JP | S62164617 A | 7/1987 | |
| JP | 2004002275 A | 1/2004 | |
| JP | 2005145876 * | 6/2005 | ............ A61K 8/06 |
| WO | 9400508 A1 | 1/1994 | |
| WO | 9614145 A1 | 5/1996 | |
| WO | 2014184658 A2 | 11/2014 | |
| WO | 2014184659 A2 | 11/2014 | |
| WO | 2014184660 A2 | 11/2014 | |

OTHER PUBLICATIONS

Falcone (The Effect of Degree of Polymerization of Silicates on Their Interactions with Cations in Solution. In Soluble Silicates; ACS Symposium Series; American Chemical Society; 1982).*

(Continued)

*Primary Examiner* — Abigail Vanhorn
*Assistant Examiner* — Jessica Kassa
(74) *Attorney, Agent, or Firm* — The Marbury Law Group, PLLC

(57) ABSTRACT

Disclosed are methods of preparing stable O/W emulsions by silicic acid complexation of micron-sized oil droplets, and stable emulsions prepared by silicic acid complexation. Compositions and products comprising the emulsions are also disclosed. Emulsions may be stable over an extended period of time at room temperature.

22 Claims, 2 Drawing Sheets

(56) References Cited

OTHER PUBLICATIONS

Pub Chem (Sodium Meta Siliciate; accessed Sep. 21, 2015).*
Armstrong et al. (Applied Microbiology vol. 2, No. 2, p. 132-137, Mar. 1964).*
Burguera et al. (Talanta 96 (2012) 11-20).*
Amphoteric Surfactants, 2nd Ed., vol. 59, Surfactant Science Series, E. G. Lomax, ed., Marcel Dekker, New York, 1996, pp. 121.
Binks B.P., et al., "Enhanced Stabilization of Emulsions Due to Surfactant-Induced Nanoparticle Flocculation," Langmuir, 2007, vol. No. 23 (14), pp. 7436-7439.
Binks B.P., et al., "Synergistic Interaction in Emulsions Stabilized by a Mixture of Silica Nanoparticles and Cationic Surfactant," Langmuir, 2007, vol. No. 23 (7), pp. 3626-3636.
Database WPI Week 198708 Thomson Scientific, London, GB; AN 1987-052881 XP002732259.
Database WPI Week 198734 Thomson Scientific, London, GB; AN 1987-240057 XP002732260.
Dickinson, et al., "Food emulsions and foams Stabilization by particles," Current Opinion in Colloid and Interface Science, London, GB, XP026896477, vol. 15, No. 1-2, (Apr. 1, 2010), pp. 40-49.
Hunter et al., "The role of particles in stabilising foams and emulsions," Advances in Colloid and Interface Science, Elsevier, NL, XP 022510900, vol. 137, No. 2, (Mar. 4, 2008), pp. 57-81.
International Search Report for Application No. PCT/IB2014/001467, dated Jan. 26, 2015, 3 pages.
International Search Report for Application No. PCT/IB2014/001485, dated Nov. 25, 2014, 4 pages.
International Search Report for Application No. PCT/IB2014/001487, dated Jan. 7, 2015, 4 pages.
Kaptay, G., "Interfacial Criteria for Stabilizing of Liquid Foams by Solid Particles," Colloids and Surfaces, A. Physicachemical and Engineering Aspects, Elsevier, Amsterdam, NL, XP008068726, vol. 230, No. 1-03, (Jan. 1, 2004), pp. 67-80.
Lherminier: "Etude mecanique et rheophysique de mousses encapsulees," (Jun. 26, 2013), XP055151733, Retrieved from the Internet: URL: http://www.ens-lyon.fr/DSM/SDMsite/M2/stages_M2/Lherminier2013.pdf [retrieved on Nov. 7, 2014], pp. 6-7.
Stamkulov, N SH et al., "Stabilisation of emulsions by using a comgination of an oil soluble ionic surfactant and water soluble polyelectrolytes. I: Emulsion stabilisation and Interfacial tension measurments," Colloids and Surfaces, A. Physicachemical and Engineering Aspects, Elsevier, Amsterdam, NL, XP026654191, vol. 335, No. 1-3, (Mar. 5, 2009), pp. 103-106.
Stocco, Antonio et al., "Particle-stabilised foams: an interfacial study," Soft Matter, XP 055163020, vol. 5, No. 11 (Jan. 1, 2009), pp. 2215-2222.
Velikov K.P., et al., "Direct Observation of the Dynamics of Latex Particles Confined inside Thinning Water-Air Films," Langmuir, 1998, vol. 14, pp. 1148-1155.
Wang, J. et al., "Synergistic stabilization of emulsions by poly(oxypropylene)diamine and Laponite particles," Colloids and Surfaces, A, Physicachemical and Engineering Aspects, Elsevier, Amsterdam, NL, vol. 353, No. 2-3, XP026806479, (Jan. 15, 2010), pp. 117-124.
Whitby, C.P. et al., "Effect of oil soluble surfactant in emulsions stabilised by clay particles," Journal of Colloid and Interface Science, Academic Press, NY, NY, vol. 323, No. 2, (Jul. 15, 2008), pp. 411-416.
International Preliminary Report on Patentability for PCT/IB2014/001485 (dated Nov. 26, 2015).
International Preliminary Report on Patentability for PCT/IB2014/001487 (dated Nov. 26, 2015).
International Preliminary Report on Patentability for PCT/IB2014/001467 (dated Nov. 26, 2015).
Pichot et al., "Mixed-Emulsifier Stabilized Emulsions: Investigation of the Effect of Monoolein and Hydrophilic Silica Particle Mixtures on the Stability Against Coalescence," Journal of Colloid and Interface Science, 329, (2009), pp. 284-291.
Menger, Fredric M et al., "Relationship Between Surface Tension and Surface Coverage," American Chemical Society, Langmuir 27,(2011), pp. 13975-13977.

* cited by examiner

EMULSION STABILIZATION VIA SILICILIC ACID COMPLEXATION

FIELD OF THE DISCLOSURE

The disclosure relates to oil-in-water ("O/W") emulsions useful in a variety of applications, and methods for preparing O/W emulsions. The O/W emulsions according to the disclosure may exhibit improved stability over an extended period of time, such as for several months, even when stored at room temperature.

BACKGROUND

Methods for preparing stable emulsions are known. For example, incorporation of a surfactant into an emulsion is a widely used technique for stabilizing an emulsion. However, as there is a desire for preparing emulsions with decreased amounts of surfactant, in order to address both safety and environmental concerns, additional techniques have been proposed.

One such method utilizes amphiphilic polymers, but this technique is limited in that it is only useful in certain emulsions where the amphiphilic polymer is compatible with the oil phase of the emulsion, or where polymer interactions do not disrupt the rheological behavior of the emulsion. A second method utilizes particles, typically inorganic, to form a Pickering emulsion as known in the state of the art. This technique likewise has drawbacks in that the particles must be carefully chosen such that they are compatible with the oil phase of the emulsion and that the properties of the particles do not adversely affect the emulsion.

Microcapsule techniques have also been proposed. For instance, U.S. Pat. Nos. 6,159,453 and 6,238,650 describe sol-gel microcapsules comprising sunscreen active ingredients; U.S. Patent Publication No. 2008/199526 describes compositions comprising two sunscreen agents encapsulated within microcapsules having a specific diameter; and U.S. Pat. No. 8,110,284 describes microcapsules having a core material encapsulated within a microcapsular shell, wherein the core material comprises an active ingredient.

Additionally, U.S. Patent Publication Nos. 2011/158923, 2011/293677, and 2011/311723 all describe silica shell techniques. These techniques have a drawback, however, in that the shell is made by a process that releases harmful by-products, which for both human and environmental safety reasons, is desired to be avoided.

In addition to avoiding the above-mentioned drawbacks, there is also a desire in certain industries, such as, for example, the food, cosmetic, and consumer chemical (e.g. household product) industries, to prepare emulsions that have certain properties, such as the ability to concentrate/dilute dispersions in water or other emulsions without interaction, to prepare emulsions that are stable even after application to a surface and/or evaporation of the water phase, particularly at room temperature, and to prepare emulsions that have slow-release properties, for instance.

Thus, there is a need for methods to prepare O/W emulsions that provide the desired properties and which can be used in a variety of applications and industries, while decreasing the use of surfactants and increasing stability of the emulsion.

SUMMARY

It has been discovered that O/W emulsions prepared via silicic acid complexation allows for the formation of a rigid interface between the oil and water phases. The oil droplets can be individually encapsulated, which may prevent coalescence or so-called Oswald-ripening, resulting in increased stability.

According to various embodiments of the disclosure, O/W emulsions can be prepared where the dispersed phase comprises oil droplets and the continuous phase comprises a surface-active material at the oil-water interface, by any method known. Separately, a solution of silicate salts is prepared and the pH adjusted so that silicic acid is produced, creating anionic complexes that are attracted to the cationic surface of the oil droplets. This process leads to encapsulation of the oil droplets, and O/W emulsions having improved stability over extended periods of time.

DESCRIPTION OF EXEMPLARY EMBODIMENTS

Figure 1:
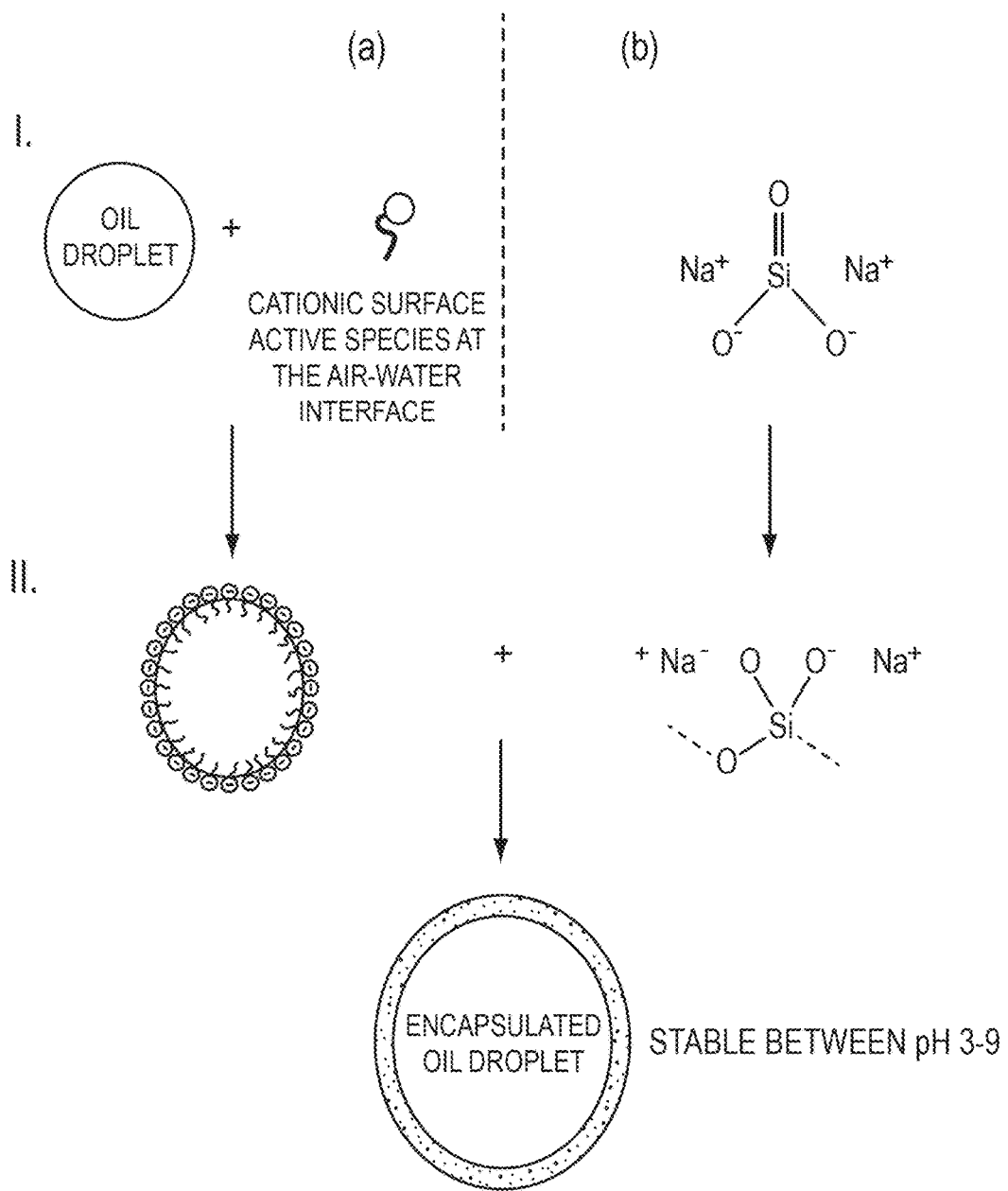
FIG. 1 is a schematic of an exemplary encapsulation process, according to an embodiment of the disclosure.

The disclosure relates to O/W emulsions prepared via silicic acid complexation, and methods of preparing such emulsions.

The encapsulation process may, in various embodiments, comprise steps of preparing an O/W dispersion, where the dispersed phase comprises oil droplets and the continuous phase comprises a surface-active material at the oil-water interface. This may be done by any method known, such as, for example, by high speed blender (e.g. ultraturax), rotor-stator, high pressure homogenizer, static mixer, in-line mixer, etc.

According to various embodiments of the disclosure, the O/W dispersion comprises, for example, about 5% to about 50%, such as about 5% to about 40%, about 10% to about 50%, about 10% to about 40%, about 15% to about 50%, about 15% to about 40%, about 5% to about 35%, about 10% to about 35%, about 15% to about 35%, such as about 20% to about 30%, of the dispersed (oil) phase, in the form of droplets.

The oil droplets of the dispersed phase may, according to various embodiments, be in the range of micron-sized. For example, the droplets may range up to about 1000 μm, such as up to about 500 μm, up to about 250 μm, or up to about 100 μm. By way of non-limiting example only, the droplets may range from about 0.05 μm to about 500 μm, such as about 0.1 μm to about 500 μm, about 0.5 μm to about 500 μm, about 1 μm to about 500 μm, about 5 μm to about 500 μm, about 0.1 μm to about 250 μm, about 0.5 μm to about 250 μm, about 1 μm to about 250 μm, about 5 μm to about 250 μm, about 0.1 μm to about 100 μm, about 0.5 μm to about 100 μm, about 1 μm to about 100 μm, or about 5 μm to about 100 μm. In further embodiments, the droplets may range up to about 50 μm, such as from about 1 μm to about 50 μm, such as about 1 μm to about 10 μm, about 5 μm to about 50 μm, about 5 μm to about 20 μm, or about 5 μm to about 10 μm.

The dispersed phase may comprise any type of natural or synthetic oil that may be useful according to the industry or application of interest. By way of non-limiting example, the oils may be chosen from triglycerides, esters, ethers, silicones, volatile oils, or combinations thereof. Further, oily compounds, such as, for example, sunscreen filters, vitamins, and lipophilic or other molecules that may be dissolved in oil may be used. As yet a further non-limiting example, milk and milk derivatives may be used, for example in food applications.

The continuous phase may be aqueous, and may comprise at least one surface active agent. By way of example only, the at least one surface active agent may be chosen from cationic surface active agents, as well as from amphoteric surface active agents or other molecules that may be pH-adjusted such that they become cationic. The at least one surface active agent may be present in an amount ranging from about 0.5 to about 50 times the Critical Micellar Concentration ("CMC") of the emulsion, such as, for example, about 0.5 to about 40 times the CMC, about 1 to about 40 times the CMC, about 1 to about 25 times the CMC, or about 1 to about 15 times the CMC.

Exemplary, non-limiting cationic surface active agents include optionally polyoxyalkylenated primary, secondary and tertiary fatty amines, quaternary ammonium salts, and mixtures thereof.

Exemplary quaternary ammonium salts may be chosen from:

those of the general formula (I) below:

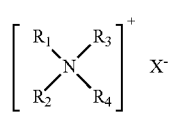

wherein R1, R2, R3, and R4, which may be identical or different, are chosen from linear and branched aliphatic radicals comprising from 1 to 30 carbon atoms, and aromatic radicals; and X— is chosen from halides, phosphates, acetates, lactates, (C2-C6) alkyl sulfates, and alkyl- or alkylaryl-sulfonates;

quaternary ammonium salts of imidazoline;

diquaternary ammonium salts of formula (II):

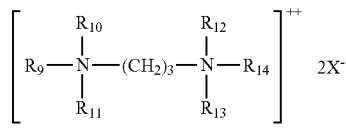

wherein R9 is chosen from aliphatic radicals comprising from 16 to 30 carbon atoms; R10, R11, R12, R13, and R14, which may be identical or different, are chosen from hydrogen and alkyl radicals comprising from 1 to 4 carbon atoms; and X— is chosen from halides, acetates, phosphates, nitrates, ethyl sulfates, and methyl sulfates; and quaternary ammonium salts comprising at least one ester function.

Exemplary and non-limiting quaternary ammonium salts of imidazoline may be chosen from those of formula (III) below:

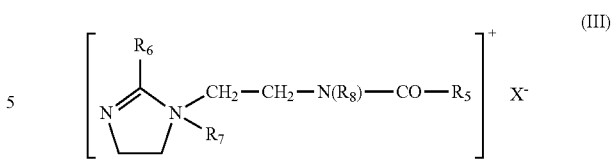

wherein R5 is chosen from alkenyl and alkyl radicals comprising from 8 to 30 carbon atoms; R6 is chosen from hydrogen, C1-C4 alkyl radicals, and alkenyl and alkyl radicals comprising from 8 to 30 carbon atoms; R7 is chosen from C1-C4 alkyl radicals; R8 is chosen from hydrogen and C1-C4 alkyl radicals; and X— is chosen from halides, phosphates, acetates, lactates, alkyl sulfates, alkyl sulfonates, and alkylaryl sulfonates.

By way of example only, the at least one cationic surfactant may be chosen from behenyltrimethylammonium chloride, cetyltrimethylammonium chloride, quaternium-83, quaternium-87, quaternium-22, behenylamidopropyl-2,3-dihydroxypropyldimethylammonium chloride, palmitylamidopropyltrimethylammonium chloride, stearamidopropyldimethylamine, and chloride and methyl sulfates of diacyloxyethyldimethylammonium, of diacyloxyethylhydroxyethylmethylammonium, of monoacyloxyethyldihydroxyethylmethylammonium, of triacyloxyethylmethylammonium, of monoacyloxyethylhydroxyethyldimethylammonium, and mixtures thereof.

For example, the at least one cationic surfactant may be chosen from caprylyl trimethyl ammonium chloride (Aliquat 2); oleyl trimethyl ammonium chloride (Aliquat 11); oleyl-linoleyl trimethyl ammonium chloride (Aliquat 15); dilauryl dimethyl ammonium chloride (Aliquat 204); lauryl heterocyclic tertiary amine (Amine C); cetyl dimethyl ethyl ammonium bromide (Ammonyx DME); cetyl dimethyl benzyl ammonium chloride (Ammonyx T); lauryl trimethyl ammonium chloride (Arquad 12-50); cetyl trimethyl ammonium chloride (Arquad 16-50); stearyl trimethyl ammonium chloride (Arquad 18-50); quaternized 2-amino pentadecane (Arquad L-15); dicoco dimethyl ammonium chloride (Arquad 2C-50); N-cetyl ethyl morpholinium ethosulfate (Atlas G 263); alkenyl dimethyl ethyl ammonium bromide (Barquat OE-50); lauryl isoquinolinium bromide (Barquat IB-75); myristyl dimethyl benzyl ammonium chloride (BTC 1750); stearamido propyl dimethyl B-hydroxyethyl ammonium phosphate (Catanac SP); tetradecyl pyridinium bromide (Fixanol VR); heptadecenyl imidazolinium bromide (Intexan HB-50); quaternary substituted imidazoline of oleic acid (Monaquat OIBC); substituted imidazoline of myristic acid (Monazoline M); coco fatty dialkyl benzyl ammonium chloride (Quatrene CB); fatty glyoxalidinium chloride (Quatrene 0-56); soya fatty dialkyl benzyl ammonium chloride (Quatrene SFB); 1-hydroxyethyl 2-heptadecenyl imidazoline hydrochloride (Romine BTQ); and lauryl dimethyl benzyl ammonium chloride (Vantoc CL).

Exemplary, non-limiting amphoteric surface active agents include derivatives of betaine, derivatives of alkylamphoacetates, derivatives of hydroxylsultaines, and mixtures thereof.

Non-limiting examples of betaine derivatives which may be used include cocobetaine, such as, for example, DEHYTON AB-30® from Cognis, laurylbetaine, such as GENAGEN KB® from Clariant, oxyethylenated laurylbetaine (10 OE), such as LAURYLETHER(10 OE)BETAINE® from Shin Nihon Rica, oxyethylenated stearylbetaine (10 OE), such as STEARYLETHER(10 OE)BETAINE® from Shin Nihon Rica, cocamidopropyl betaine, such as VELVETEX BK 35® from Cognis, and undecylenamidopropyl betaine, such as AMPHORAM U® from Ceca.

Exemplary and non-limiting alkylamphoacetate derivatives include N-cocoyl-N-carboxymethoxyethyl-N-carboxymethyl-ethylenediamine N-di-sodium (INCI name: disodium cocamphodiacetate), such as MIRANOL C2M CONCENTRE NP® from Rhodia Chimie, and N-cocoyl-N-hydroxyethyl-N-carboxymethyl-ethylenediamine N-sodium (INCI name: sodium cocamphoacetate).

Exemplary, non-limiting derivatives of hydroxylsultaines that may be used include Cocamidopropyl hydroxysultaine, such as that sold as REWOTERIC AM® by Golschmidt-Degussa.

The continuous phase may optionally further comprise any additional component that may be desired in the final emulsion, depending on the ultimate intended application. By way of non-limiting example only, the continuous phase may optionally further comprise at least one humectant, sugar, polymer, peptide, UV absorber, sunscreen, dye, etc. In yet further exemplary embodiments, the continuous phase may comprise lipophilic active agents or lipophilic active compounds: retinol (vitamin A) and derivatives thereof, tocopherol (vitamin E) and derivatives thereof, essential oils or unsaponifiable materials (e.g., bergamot, tocotrienol, sesamine, gamma-oryzanol, phytosterols, squalenes, waxes and terpenes), ascorbyl palmitate, vitamin F glycerides, D vitamins, vitamin D2, vitamin D3, retinol, retinol esters, retinyl palmitate, retinyl propionate, carotenes including beta-carotene, D-panthenol, farnesol, farnesyl acetate, salicylic acid and compounds thereof, for instance 5-n-octanoylsalicylic acid, alkyl esters of alpha-hydroxy acids such as citric acid, lactic acid, glycolic acid, asiatic acid, madecassic acid, asiaticoside, the total extract of *Centella asiatica*, beta-glycyrrhetinic acid, alpha-bisabolol, ceramides, for instance 2-oleoylamino-1,3-octadecane, phytanetriol, phospholipids of marine origin rich in polyunsaturated essential fatty acids, ethoxyquine, rosemary extract, balm extract, quercetin, extract of dried microalgae, octyl methoxycinnamate, butylmethoxydibenzoylmethane, octyl triazone, 3,5-di-tert-butyl-4-hydroxy-3-benzylidenecamphor, antibiotics, antifungal agents, anaesthetics, analgesics, antiseptics, antiviral agents, pesticides and herbicides, and mixtures thereof. One of skill in the art will be able to select both the type and amount of optional additional component in order to avoid degradation of the emulsion.

For example, in at least certain embodiments, the continuous phase may optionally comprise at least one lipophilic active agent or compounds. Non-limiting examples include retinol (vitamin A) and derivatives thereof, tocopherol (vitamin E) and derivatives thereof, essential oils or unsaponifiable materials (e.g., bergamot, tocotrienol, sesamine, gamma-oryzanol, phytosterols, squalenes, waxes and terpenes), ascorbyl palmitate, vitamin F glycerides, D vitamins, vitamin D2, vitamin D3, retinol, retinol esters, retinyl palmitate, retinyl propionate, carotenes including beta-carotene, D-panthenol, farnesol, farnesyl acetate, salicylic acid and compounds thereof, for instance 5-n-octanoylsalicylic acid, alkyl esters of alpha-hydroxy acids such as citric acid, lactic acid, glycolic acid, asiatic acid, madecassic acid, asiaticoside, the total extract of *Centella asiatica*, beta-glycyrrhetinic acid, alpha-bisabolol, ceramides, for instance 2-oleoylamino-1,3-octadecane, phytanetriol, phospholipids of marine origin rich in polyunsaturated essential fatty acids, ethoxyquine, rosemary extract, balm extract, quercetin, extract of dried microalgae, octyl methoxycinnamate, butylmethoxydibenzoylmethane, octyl triazone, 3,5-di-tert-butyl-4-hydroxy-3-benzylidenecamphor, antibiotics, antifungal agents, anaesthetics, analgesics, antiseptics, antiviral agents, pesticides and herbicides, and mixtures thereof.

Separately, a solution of silicate salts can be prepared by any method known. The solution may optionally be an aqueous solution, and may comprise any silicate salt soluble in the solvent, such as, by way of non-limiting example, disodium silicate ($Na_2SO_3$), calcium silicate, magnesium silicate, sodium silicate, aluminum silicate, potassium silicate, zirconium silicate, tetramethylammonium silicate, sodium alumino silicate, potassium methyl siliconate, sodium methyl siliconate, and mixtures thereof.

According to various embodiments of the disclosure, the silicate salt solution may comprise an amount of at least one silicate salt in an amount sufficient to prepare a solution having a concentration ranging from about 0.05 to about 0.3 M, such as about 0.08 to about 0.3 M, about 0.05 to about 0.2 M, or about 0.08 to about 0.2 M.

Once the solution comprising at least one silicate salt is prepared, the pH may be adjusted so that silicic acid is produced. The pH may be adjusted by any method known in order to achieve a final pH in the range of about 6.0 to about 10.0, such as about 6.5 to about 9.0, about 6.5 to about 8.5, or about 7.0 to about 8.0.

After the pH of the silicate solution is adjusted, the solution may be mixed with the O/W dispersion in a desired ratio. For example, the ratio of silicate solution:O/W dispersion may range from about 20:80 to about 80:20, such as about 40:60 to about 60:40, or about 50:50.

Upon mixing, encapsulation of the oil droplets occurs substantially immediately and completely. Without wishing to be bound by theory, it is believed that adsorption of the surface-active material to the oil-water interface in the O/W dispersion renders it positively charged. Then, the process of adjusting the pH of the silicate salt solution creates anionic complexes that are thus attracted to the cationic surface of the oil droplets upon mixing. It should be noted, however, that in at least certain embodiments, encapsulation may not occur substantially immediately or completely, yet such embodiments are intended to be within the scope of the disclosure.

As can be seen in FIG. 1, which is a schematic of an exemplary method of encapsulating oil droplets according to an embodiment of the disclosure, in I(a), an oil dispersion in the form of micron-sized oil droplets is combined with an aqueous solution comprising at least one cationic surface active agent. In II(a), the at least one cationic surface active agent is adsorbed onto the oil droplet, rendering it positively charged. In I(b), a silicate salt solution comprising sodium meta-silicate is prepared, and in II(b), the silicate salt solution is pH adjusted, after which, the oil-in-water dispersion and silicate salt solution are combined, resulting in an encapsulated oil droplet.

Methods for preparing encapsulated oil droplets, and emulsions comprising encapsulated oil droplets, according to embodiments of the disclosure may be useful for preparing O/W emulsions for use in a variety of industries, such as, by way of non-limiting example, food, personal care (e.g. cosmetic, dermatological, perfume, etc.), pharmaceutical, and consumer chemical (e.g. household products). It may also be possible to incorporate O/W emulsions prepared according to embodiments of the disclosure into compositions or emulsions (e.g. O/W, W/O, W/O/W, etc.) for use in a variety of industries, such as, by way of non-limiting example, food, personal care (e.g. cosmetic, dermatological, perfume, etc.), pharmaceutical, and consumer chemical (e.g. household products). As such, compositions, emulsions, and products comprising O/W emulsions according to embodiments of the disclosure, or comprising oil droplets encapsulated according to embodiments of the disclosure, are further intended to be within the scope of the disclosure.

In at least certain exemplary embodiments according to the disclosure, the compositions, emulsions, and products comprising oil droplets encapsulated according to various embodiments of the disclosure may be stable for a period of several months, such as up to about 24 months, up to about 18 months, up to about 12 months, or up to about 6 months, at room temperature. It should be noted, however, that stability may vary according to various embodiments of the disclosure, and/or compositions, emulsions, and/or products made according to embodiments described herein may not offer improved stability over an extended period of time, yet such embodiments are intended to be within the scope of the disclosure.

As described herein, steps of various processes and procedures are listed in a certain order. However, it is to be understood that, unless explicitly stated otherwise, the order of performing the steps in the processes or procedures is not critical, and thus, processes and procedures having the specified steps, but in a different order, are likewise intended to be within the scope of the disclosure.

Unless otherwise indicated, all numbers used in the specification and claims are to be understood as being modified in all instances by the term "about," whether or not so stated. It should also be understood that the precise numerical values used in the specification and claims form additional embodiments of the invention, and are intended to include any ranges which can be narrowed to any two end points disclosed within the exemplary ranges and values provided. Efforts have been made to ensure the accuracy of the numerical values disclosed herein. Any measured numerical value, however, can inherently contain certain errors resulting from the standard deviation found in its respective measuring technique.

All patents and published applications mentioned herein are incorporated by reference in their entireties.

EXAMPLE

The following Example is intended to be non-restrictive and explanatory only, with the scope of the invention being defined by the claims.

Example

Stable Emulsion

An aqueous solution of cetyl trimethyl ammonium chloride surfactant was prepared having 4 times the CMC (4.0 mM). An oil phase (20% of the total composition) composed of 5% of isononyl isononanoate, 10% of sarcosine lauroyl isopropyl, and 5% isocetyl stearate was prepared and mixed with the aqueous solution to generate an O/W dispersion.

An aqueous solution of $Na_2SiO_3$ solution (0.18 M) was prepared (pH was about 12). The pH was adjusted to about 8.5 using an HCl solution (4.6 mL of HCl 23 wt % per 100 mL $Na_2SiO_3$ solution).

Immediately after the pH of the $Na_2SiO_3$ solution was adjusted, the O/W dispersion and $Na_2SiO_3$ solution were mixed 50:50 by volume.

Figure 2:
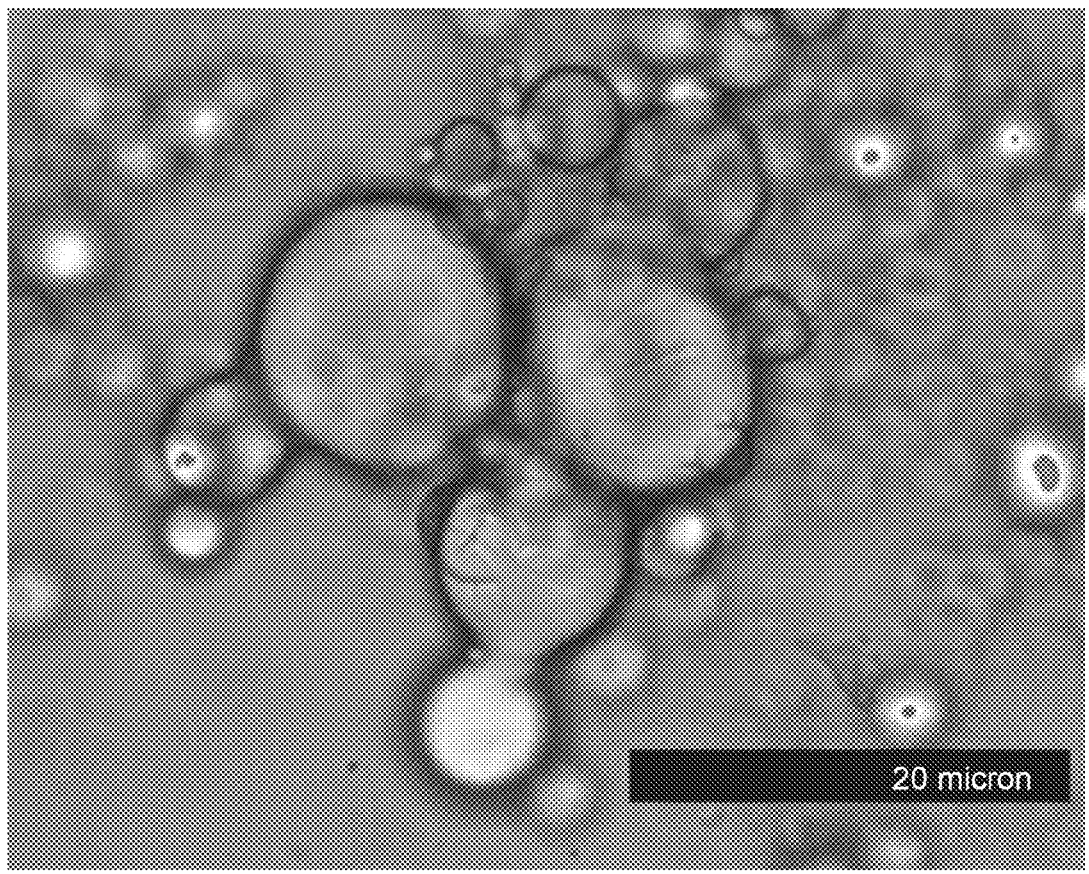
FIG. 2 is a micrograph showing encapsulated oil droplets prepared according to an exemplary embodiment of the disclosure.

Encapsulation of the oil droplets was seen substantially immediately, although it was also noted that there was an excess of $Na_2SiO_3$ solution which gelled in the bulk excess solution. A micrograph of the encapsulated oil droplets can be seen in FIG. 2. The emulsion was kept at pH 6 at room temperature (23° C., ±5° C.) for over two years, and remained stable.

What is claimed is:

1. A method for preparing an emulsion, said method comprising:
   preparing an O/W dispersion comprising at least one cationic surface active adsorbed to the oil-water interface such that oil droplets have a cationic surface;
   preparing a solution comprising at least one dissolved silicate salt;
   adjusting the pH of the solution comprising the at least one dissolved silicate salt to a range of from about 6.0 to about 9.0 to create anionic complexes;
   mixing the O/W dispersion and the solution comprising at least one dissolved silicate salt such that the anionic complexes are attracted to the cationic surface of the oil droplets, resulting in encapsulated oil droplets.

2. The method according to claim 1, wherein the size of the oil droplets ranges from about 0.1 µm to about 500 µm.

3. The method according to claim 1, wherein the volume of the oil phase in the O/W dispersion ranges from about 5% to about 50%.

4. The method according to claim 1, wherein the oil phase comprise at least one oil chosen from triglycerides, esters, ethers, silicones, and volatile oils, or at least one oily compound chosen from sunscreen filters, vitamins, and lipophilic molecules dissolved in oil.

5. The method according to claim 1, wherein the concentration of the at least one cationic surface active agent ranges from about 1 to about 25 times Critical Micellar Concentration.

6. The method according to claim 1, wherein the at least one cationic surface active agent is chosen from optionally polyoxyalkylenated primary, secondary and tertiary fatty amines, quaternary ammonium salts, and mixtures thereof.

7. The method according to claim 1, wherein the at least one cationic surface active agent is chosen from at least one amphoteric surface active agent that has been pH-adjusted to be cationic.

8. The method according to claim 7, wherein the at least one cationic surface active agent chosen from at least one amphoteric surface active agent that has been pH-adjusted to be cationic is chosen from derivatives of betaine, derivatives of alkylamphoacetate, derivatives of hydroxylsultaines, and mixtures thereof.

9. The method according to claim 1, wherein the solution comprising at least one silicate salt has a concentration ranging from about 0.05 M to about 0.3 M.

10. The method according to claim 1, wherein the at least one silicate salt is chosen from disodium silicate, calcium silicate, magnesium silicate, sodium silicate, aluminum silicate, potassium silicate, zirconium silicate, tetramethylammonium silicate, sodium alumino silicate, potassium methyl siliconate, sodium methyl siliconate, and mixtures thereof.

11. The method according to claim 1, wherein mixing the O/W dispersion and the solution comprising the at least one silicate salt comprises mixing the O/W dispersion and the solution comprising at a ratio of silicate solution: O/W dispersion ranging from about 20:80 to about 80:20.

12. A method for preparing an emulsion, said method comprising the steps of:
   a. preparing an aqueous solution having at least one cationic surface active agent;
   b. preparing an oil phase;

c. mixing said aqueous solution having at least one cationic surface active agent and said oil phase to obtain an O/W dispersion comprising oil droplets having a cationic surface;

d. preparing a solution comprising at least one dissolved silicate salt;

e. adjusting the pH of the solution comprising the at least one dissolved silicate salt to a range of from about 6.0 to about 9.0 to create anionic complexes; and f. mixing the O/W dispersion and the solution comprising the at least one dissolved silicate salt such that the anionic complexes are attracted to the cationic surface of the oil droplets, resulting in encapsulated oil droplets.

13. The method according to claim 12, wherein the size of the oil droplets ranges from about 0.1 μm to about 500 μm.

14. The method according to claim 12, wherein the volume of the oil phase in the O/W dispersion ranges from about 5% to about 50%.

15. The method according to claim 12, wherein the oil phase comprise at least one oil chosen from triglycerides, esters, ethers, silicones, and volatile oils, or at least one oily compound chosen from sunscreen filters, vitamins, and lipophilic molecules dissolved in oil.

16. The method according to claim 12, wherein the concentration of the at least one cationic surface active agent ranges from about 1 to about 25 times Critical Micellar Concentration.

17. The method according to claim 12, wherein the at least one cationic surface active agent is chosen from optionally polyoxyalkylenated primary, secondary and tertiary fatty amines, quaternary ammonium salts, and mixtures thereof.

18. The method according to claim 12, wherein the at least one cationic surface active agent is chosen from at least one amphoteric surface active agent that has been pH-adjusted to be cationic.

19. The method according to claim 18, wherein the at least one cationic surface active agent chosen from at least one amphoteric surface active agent that has been pH-adjusted to be cationic is chosen from derivatives of betaine, derivatives of alkylamphoacetate, derivatives of hydroxylsultaines, and mixtures thereof.

20. The method according to claim 12, wherein the solution comprising at least one silicate salt has a concentration ranging from about 0.05 M to about 0.3 M.

21. The method according to claim 12, wherein the at least one silicate salt is chosen from disodium silicate, calcium silicate, magnesium silicate, sodium silicate, aluminum silicate, potassium silicate, zirconium silicate, tetramethylammonium silicate, sodium alumino silicate, potassium methyl siliconate, sodium methyl siliconate, and mixtures thereof.

22. The method according to claim 12, wherein mixing the O/W dispersion and the solution comprising the at least one silicate salt comprises mixing the O/W dispersion and the solution comprising at a ratio of silicate solution: O/W dispersion ranging from about 20:80 to about 80:20.

* * * * *